United States Patent [19]

Van Wezel

[11] Patent Number: 4,508,708
[45] Date of Patent: Apr. 2, 1985

[54] VIRUS VACCINES AND PROCESS FOR PREPARING THE SAME

[75] Inventor: Antonius L. Van Wezel, Bilthoven, Netherlands

[73] Assignee: De Staat Der Nederlanden, Vertegenwoozdigd doozde Minister van volksgezondheid en Milieuhygiene, BaLeidschendam, Netherlands

[21] Appl. No.: 384,386

[22] Filed: Jun. 2, 1982

[30] Foreign Application Priority Data

Jun. 5, 1981 [NL] Netherlands .......................... 8102740

[51] Int. Cl.$^3$ .................... A61K 39/13; A61K 39/135
[52] U.S. Cl. ....................................... 424/89; 435/238
[58] Field of Search ............................ 424/89; 435/238

[56] References Cited

U.S. PATENT DOCUMENTS

4,140,763  2/1979  Bachrach .

FOREIGN PATENT DOCUMENTS

0018199  10/1980  European Pat. Off. .
1443612  7/1976  United Kingdom .

OTHER PUBLICATIONS

McSharry et al, C.A. 91, #204276h, (1979), of Virology, (1979), 97(2): 307–315, Inhibition of Uncoating of Poliovirus by Arildone a New Antiviral Drug.
Kim et al, C.A. 93, #197596y, (1980), of Antimicrob. Agents Chemother., (1980), 18(2): 276–280, Antiviral Activity of Arildone on DNA and RNA Viruses.
Caliguiri et al, C.A. 93, #180170g, (1980), of Virology, (1980), 105(1): 86–93, Effect of Arildone on Modifications of Poliovirus in Vitro.
Schrom et al, C.A. 97, #212568u, (1982), of Virology, (1982), 122(2): 492–7, Isolation of Poliovirus Variants Resistant to and Dependent on Arildone.
McKinlay et al, C.A. 98, #46519c, (1983), of Antimicrobial Agents Chemother. (1982), 22(6): 1022–5, Prevention of Human Poliovirus–Induced Paralysis and Death in Mice by Antiviral Arildone.
Van Wezel et al, C.A. 98, #132294g, (1983), of Eur. Pat. Appl., EP66932, 15 Dec. 1982, Virus Vaccines.
Kuhrt et al, C.A. 91, #84052h, (1979), of Antimicrob. Agents Chemother., (1979), 15(6): 813–819, Preliminary Studies of the Mode of Action of Arildone a Novel Antiviral Agent.
McSharry et al, C.A. 98, #18k, (Jan. 3, 1983), of Handb. Exp. Pharmacol. 1982, (61 Chemother. Viral Infect.), 419–444, Arildone: A B-Diketone.
Nature, vol. 227, Aug. 15, 1970, pp. 680–685.
Antimicrob. Agents Chemother, 15, (1979), 813–819.
Develop. Biol. Standard, 41, (1978), 159–168.
J. Gen. Virol., 45, (1979), 761–763.
Develop. Biol. Standard, 47, (1981), 101–108.
Caligurin, Virology, vol. 105, pp. 86–92, (1980).

*Primary Examiner*—Shep K. Rose
*Attorney, Agent, or Firm*—Cushman, Darby & Cushman

[57] ABSTRACT

The invention relates to virus vaccines and to a process for the preparation thereof especially to polio virus vaccines and other picorna virus vaccines, such as foot-and-mouth disease vaccine.

The invention provides vaccines which are stabilized and show an improved activity by the addition of compounds of formula I of the formula sheet, in which $R_1$ en $R_2$ each represent an alkyl- or alkoxy group of not more than 6 carbon atoms, preferably not more than 4 carbon atoms, A represents a bivalent hydrocarbon radical of 3–12 carbon atoms, $R_3$ represents an unsubstituted or substituted phenyl radical and n is 1 or 0.

24 Claims, 4 Drawing Figures

1
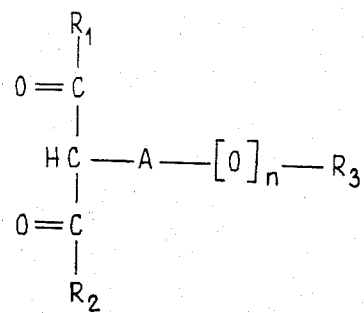
2
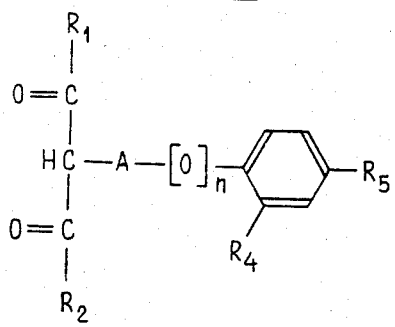
3
4
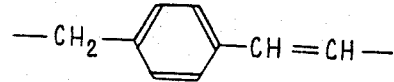

VIRUS VACCINES AND PROCESS FOR PREPARING THE SAME

The invention relates to virus vaccines and to a process for the preparation thereof especially to polio virus vaccines and other picorna virus vaccines, such as foot-and-mouth disease vaccine.

It was found that compounds of formula 1 of the formula sheet, in which $R_1$ and $R_2$ each represent an alkyl or alkoxy group of not more than 6 carbon atoms, preferably not more than 4 carbon atoms, A represents a bivalent hydrocarbon radical of 3–12 carbon atoms, $R_3$ represents an optionally substituted phenyl radical and n represents one of the figures 0 or 1, exhibit a stabilizing and adjuvant activity on virus vaccines.

The bivalent hydrocarbon radical A may be, for example, a straight or branched alkylene radical, which may also contain one or more double bonds. Also the radical A may be a cyclic hydrocarbon radical or may contain a cyclic hydrocarbon radical. This cyclic hydrocarbon radical may be aromatic, especially a 1,4-phenylene radical or a wholly or partially saturated aromatic hydrocarbon radical, especially a 1,4-cyclohexylene radical.

The radical $R_3$ is an optionally substituted phenyl radical. As possible substituents, of which 1–5 may be present in the phenyl radical, the following may be mentioned: optionally substituted alkyl, alkylmercapto and alkoxy groups, the substituents of which may be, for example, halogen atoms, hydroxyl groups, and optionally substituted amino groups; hydroxyl, alkylenedioxy, amino, alkylamino, dialkylamino, acylamino, aryl, aralkyl, aryloxy, aralkoxy, carboxy, esterified carboxy, acyl, acyloxy, and optionally substituted sulphamoyl groups.

The above described compounds are known or may be prepared in a known way. (See J. Med. Chem. 20 (1977), pages 750–756 and 757–761). It is also known from the last mentioned publications that these compounds possess an inhibiting activity on the multiplication of viruses. From the mentioned group of compounds the 4-[6-(2-chloro-4-methoxyphenoxy)hexyl]3,5-heptanedione (Arildone; formula 1, in which $R_1=R_2=-C_2H_5$; $A=-(CH_2)_6-$; $n=1$ en $R_3=$2-chloro-4-methoxyphenyl) has been studied in more detail. It appeared that this compound inhibits the multiplication of virus by blocking the removal of the virus capside (see Virology 97 (1979) 307–315; Virology 105 (1980), 86–93; and Antimicrob. Agents Chemother. 15 (1979), 831–819). This was the case with polio virus type 2 and herpes virus type 2.

According to the invention the above mentioned compounds are used in an entirely different way, namely as stabilizers and adjuvants for virus antigens. These antigens may be attached to inactivated virus, but the above mentioned compounds are also active as stabilizers and adjuvants of vaccines containing as antigen one or more polypeptides derived from viruses. Consequently, the invention is entirely different from the known use as agents inhibiting the infectivity of the virus, as the present invention relates to vaccines containing inactivated virus or polypeptides derived therefrom which accordingly, do not produce virus infection.

Consequently the invention relates to a virus vaccine being free from live virus and containing one or more virus antigens and at least one of the above defined compounds.

The drawing shows the formulae of the compounds used in the invention with formula 1 being the generic formula, formula 2, the preferred subgenus, and formulae 3 and 4 representing the preferred form for A.

The best results have been obtained with compounds of formula 1 in which $R_1$ and $R_2$ each represent an alkyl or alkoxy group of one or two carbon atoms, A represents a straight alkylene radical of six or seven carbon atoms and $R_3$ represents a phenyl radical substituted with one or more halogen atoms, alkoxy or nitro groups. Therefore, the vaccines according to the invention preferably contain one or more of these compounds, more especially compounds of formula 1, in which $R_1$ and $R_2$ each represent an ethyl group, A represents the hexamethylene radical and $R_3$ represents the 2-chloro-4-methoxyphenyl radical.

Generally the vaccines according to the invention contain at least 0.1 μg/ml of a compound of formula 1, especially about 1 μg/ml.

Good results have been obtained with inactivated poliomyelitis vaccine which may be prepared according to a method which has been developed by Salk and has been improved later in several aspects. Generally, these vaccines contain a mixture of inactivated polio virus of strains Mahoney, $MEF_1$ and Saukett. [15th IABS Congress: Vaccinations in the Developing countries, La Guadeloupe 1978, Develop. biol. Standard., 41 (1978), pages 159–168]. An especially interesting use of the invention resides in the addition of a compound according to the invention to vaccines containing as antigens polio virus polypeptides (VP's). Such polypeptides may be obtained by treating a virus suspension with one or more desintegrating agents, such as urea, sodium dodecyl sulphate and/or mercaptoethanol, thereby liberating these polypeptides, that is to say the proteins of the virus capsid. The individual virus polypeptides may be separated from each other by means of polyacrylamide gel electrophoresis (PAAGE) in the presence of one or more of the above mentioned desintegration agents or column chromatographic separation methods. Four different polypeptides have been isolated from polio virus as well as from foot-and-mouth disease virus. These are designated as $VP_1$, $VP_2$, $VP_3$ and $VP_4$. It appears from J. gen. Virol. 45 (1979), 761–763 that the individual polypeptides of polio virus are not capable to raise neutralizing antibodies in humans and animals and that, among the individual polypeptides of the foot-and-mouth disease virus, only $VP_1$ possesses this capability. As was presently found the individual polypeptides of polio virus do show a priming effect with respect to the D-antigen, the antigen assumed to be responsable for the induction of neutralizing antibodies in humans and animals. Surprisingly it was found that, after addition of one of the above mentioned compounds of formula 1, neutralizing antibodies may be raised with the individual polypeptides. Therefore, the invention also relates to vaccines in which the antigens are present in the form of one or more virus polypeptides, especially the polio virus polypeptides $VP_1$, $VP_2$, $VP_3$ and/or $VP_4$. In principle, it is possible to prepare these polypeptides by synthesis or by means of recombinant DNA techniques.

Also, the invention relates to a process for preparing virus vaccines in which a compound of formula 1, as defined above, is added to a suspension or a solution of one or more virus antigens and, when live virus is present, this is inactivated.

As, generally, the compounds of formula 1 show a very low solubility in water it is, in most cases, necessary to dissolve the substance in a co-solvent. As co-solvents water-miscible and physiological acceptable solvents exhibiting no harmful effects on the vaccine may be used. Preferably, a compound of formula 1 is dissolved in dimethylsulphoxide in a concentration of e.g. 10 mg/ml. This solution may be used, if desired after dilution, for addition to the vaccine so as to obtain the desired concentration of the additive of formula 1. As stated above, this concentration is, preferably, at least 0.1 μg/ml, especially about 1 μg/ml.

The compound of formula 1 may be added to a virus suspension before or after the inactivation, as it appeared that the presence of a substance of formula 1 does not disturb the inactivation process and has no harmful influence on the antigen titer thereof.

The compounds according to the invention act as stabilizers for virus antigens and also as adjuvants, that is to say that the compounds of formula 1 provoke an increase of the antibody titers induced by the virus vaccines.

The stabilizing activity of the compounds of formula 1 appears from the test results stated in tables, A, B, C and D.

Table A relates to the stabilizing effect of some of the compounds of formula 1 on polio virus D-antigen. The vaccine tested was of the type 1 Mahoney to which in all cases 1 μg/ml of a compound of formula 1 stated in table A had been added. The D-antigen titer of the starting material was 345 DU/ml, which titer decreased to 38 DU/ml after 46 hours incubation at 45° C. (without additive).

Arildone (compound 16 of table A) was used in the tests the results of which have been stated in tables B, C and D. Tables show that the stabilizing activity of this substance has the highest effect with the polio virus, type 1 vaccine, although the substance is also active with vaccines of type 2 and 3. All essays of the D-antigen titers were carried out with the gel diffusion or ELISA method (Develop. biol. Standard 47 (1981), 101).

Table E shows that addition of Arildone to a virus suspension before inactivation with formalin has no harmful effect on the inactivation, and has a stabilizing activity on the D-antigen as well.

Table F relates to the effect of the addition of a compound of formula 1 (Arildone) to trivalent polio vaccine on the immunogenity in rats. Especially with type 1 the serum titers provoked by the vaccine to which Arildone has been added appear to be significantly higher than with polio vaccine to which Arildone has not been added.

Table G shows that addition of 1 μg/ml of Arildone to polio type 1 vaccine gives longer lasting and higher neutalization titers in monkeys than the corresponding vaccine to which Arildone has not been added.

Finally, table H shows that among the virion polypeptides $VP_1$, $VP_2$ and $VP_3$ of polio virus type 2 $MEF_1$, only the $VP_3$ is capable of inducing neutralizing antibodies, although the antibody titer is only low. However, all of the polypeptides possess the property of increasing the function of neutralizing antibodies of D-antigen type 2. This is the priming effect mentioned above. The most important conclusion to be drawn from table H is, however, that $VP_1$, $VP_2$ and $VP_3$ are capable of inducing neutralizing antibodies when the immunisation is carried out with a preparation containing Arildone as well.

TABLE A

Stabilizing effect on polio virus D-antigen

| Test vaccine | type 1 Mahoney |
|---|---|
| Incubation | 46 h at 45° C. |
| Assay method D-antigen | ELISA |
| D antigen titer starting material | 345 DU/ml |
| Stabiliser concentration | 1 μg/ml |

Compound of formula 2, in which:

| number | $R_1$ | $R_2$ | A | $R_4$ | $R_5$ | n | DU/ml after 46 h at 45° C. |
|---|---|---|---|---|---|---|---|
| 1 | $CH_3$ | $CH_3$ | $-(CH_2)_7-$ | Cl | $OCH_3$ | 1 | 264 |
| 2 | $CH_3$ | $CH_3$ | $-(CH_2)_8-$ | Cl | $OCH_3$ | 1 | 172 |
| 3 | $CH_3$ | $CH_3$ | $-(CH_2)_9-$ | Cl | $OCH_3$ | 1 | 124 |
| 4 | $OC_2H_5$ | $CH_3$ | $-(CH_2)_9-$ | Cl | $OCH_3$ | 1 | 124 |
| 5 | $C_2H_5$ | $C_2H_5$ | $-(CH_2)_4-$ | Cl | $OCH_3$ | 1 | 158 |
| 6 | $CH_3$ | $CH_3$ | $-(CH_2)_4-$ | Cl | $OCH_3$ | 1 | 110 |
| 7 | $C_2H_5$ | $C_2H_5$ | $-(CH_2)_{10}-$ | Cl | $OCH_3$ | 1 | 94 |
| 8 | $OC_2H_5$ | $CH_3$ | $-(CH_2)_6-$ | Cl | $OCH_3$ | 1 | 246 |
| 9 | $OC_2H_5$ | $OC_2H_5$ | $-(CH_2)_6-$ | Cl | $OCH_3$ | 1 | 215 |
| 10 | $C_2H_5$ | $C_2H_5$ | $-(CH_2)_6-$ | $NO_2$ | $OCH_3$ | 1 | 242 |
| 11 | $C_2H_5$ | $C_2H_5$ | $-(CH_2)_7-$ | Cl | $OCH_3$ | 1 | 229 |
| 12 | $C_2H_5$ | $C_2H_5$ | $-(CH_2)_6-$ | H | OH | 1 | 97 |
| 13 | $C_2H_5$ | $C_2H_5$ | $-(CH_2)_6-$ | H | OH | 0 | 100 |
| 14[1] | $C_2H_5$ | $C_2H_5$ | formula 3 | Cl | $OCH_3$ | 1 | 102 |
| 15 | t.Bu | t.Bu | $-(CH_2)_6-$ | Cl | $OCH_3$ | 1 | 112 |
| 16[2] | $C_2H_5$ | $C_2H_5$ | $-(CH_2)_6-$ | Cl | $OCH_3$ | 1 | 275 |
| 17[1] | $C_2H_5$ | $C_2H_5$ | formula 4 | Cl | OH | 0 | 189 |
| 18[1] | $C_2H_5$ | $C_2H_5$ | formula 4 | H | OH | 0 | 132 |
| Control | | | | | | | 88 |

[1] trans form
[2] Arildone

TABLE B

Stability of polio D-antigen type 1, 2 and 3 at 56° C. with and without addition of Arildone.

| Type | Arildone μg/ml | DU/ml 4° C. | DU/ml 5 min. 56° C. |
|---|---|---|---|
| 1 | 0 | 1560 | 24 |
| 1 | 1 | 1440 | 120 |
| 2 | 0 | 786 | 16 |
| 2 | 1 | 810 | 492 |
| 3 | 0 | 656 | 38 |
| 3 | 1 | 670 | 250 |

TABLE C

Stability of polio type 1, 2 and 3 D-antigen in trivalent polio vaccine at 45° C. with and without addition of Arildone.

| Vaccine | type | Arildone μg/ml | DU/ml after incubation at 45° C. | | | |
|---|---|---|---|---|---|---|
| | | | 0 h | 8 h | 24 h | 48 h |
| PU 78-02 | 1 | 0 | 565 | 297 | 165 | 165 |
| | 1 | 1 | 551 | 565 | 437 | 307 |
| PU 78-02 | 2 | 0 | 48 | 48 | 48 | 44 |
| | 2 | 1 | 58 | 52 | 51 | 52 |
| PU 78-02 | 3 | 0 | 119 | 127 | 130 | 113 |
| | 3 | 1 | 152 | 141 | 141 | 136 |

TABLE D

Stability of polio type 1, 2 and 3 D-antigen in trivalent polio vaccine at +37° C. with and without addition of Arildone.

| Vaccine | type 1 | Arildone μg/ml | DU/ml after incubation at 37° C. | | | |
|---|---|---|---|---|---|---|
| | | | 0 w | 1 w | 2 w | 4 w |
| PU 78-02 | 1 | 0 | 660 | 552 | 396 | 165 |
| | 1 | 1 | 649 | 649 | 565 | 444 |
| PU 78-02 | 2 | 0 | 40 | 42 | 40 | 37 |

TABLE D-continued

Stability of polio type 1, 2 and 3 D-antigen in trivalent polio vaccine at +37° C. with and without addition of Arildone.

| Vaccine | type | Arildone µg/ml | DU/ml after incubation at 37° C. | | | |
|---|---|---|---|---|---|---|
| | | | 0 w | 1 w | 2 w | 4 w |
| PU 78-02 | 2 | 1 | 39 | 41 | 41 | 39 |
| | 3 | 0 | 169 | 166 | 151 | 151 |
| | 3 | 1 | 168 | 169 | 157 | 151 |

TABLE E

Effect of addition of 1 µg/ml of Arildone to polio virus type 1 on the inactivation of the virus with formalin 1/4000 at 37° C.

| virus suspension | 1 µg/ml Arildone | | without Arildone | |
|---|---|---|---|---|
| | log TCID$_{50}$ | DU/ml | log TCID$_{50}$ | DU/ml |
| starting suspension | 9.45 | 1560 | 9.43 | 1630 |
| + formalin 0 d 37° C. | 9.29 | 1560 | 8.71 | n.t.' |
| + formalin 1 d 37° C. | 5.63 | 1537 | 5.63 | n.t. |
| + formalin 2 d 37° C. | 3.00 | 1560 | 3.17 | n.t. |
| + formalin 3 d 37° C. | 0.71 | 1560 | <−0.05 | n.t. |
| + formalin 4 d 37° C. | <−0.05 | 1595 | <−0.05 | n.t. |
| + formalin 10 d 37° C. | n.t. | 1560 | n.t. | 1530 |
| + formalin 13 d 37° C. | n.t. | 1710 | n.t. | 1424 |

'n.t. = not tested.

TABLE F

Effect of addition of Arildone to trivalent polio vaccine on the immunogenity in rats.

| incubation at 37° C. | dilution | Arildone µg/ml | neutralisation titer[1] | | |
|---|---|---|---|---|---|
| | | | type 1 | type 2 | type 3 |
| 0 W | 1:5 | 0 | 4.9 | 8.3 | 6.9 |
| 0 W | 1:10 | 0 | 3.2 | 5.9 | 4.4 |
| 0 W | 1:20 | 0 | 2.9 | 5.0 | 3.5 |
| 1 W | 1:5 | 0 | 4.9 | 7.7 | 5.9 |
| 2 W | 1:5 | 0 | 3.2 | 8.5 | 6.0 |
| 4 W | 1:5 | 0 | 1.1 | 8.1 | 6.6 |
| 0 W | 1:5 | 1 | 5.7 | 8.1 | 5.5 |
| 0 W | 1:10 | 1 | 4.3 | 6.5 | 5.1 |
| 0 W | 1:20 | 1 | 3.1 | 6.7 | 4.7 |
| 1 W | 1:5 | 1 | 5.7 | 8.1 | 6.7 |
| 2 W | 1:5 | 1 | 5.3 | 8.4 | 5.8 |
| 4 W | 1:5 | 1 | 1.2 | 8.3 | 5.4 |

[1] $^2$log serum dilution; mean titer for two rats.

TABLE G

Effect of addition of 1 µg/ml of Arildone to polio type 1 vaccine on the immunogenity in monkeys.

| Blood drawn after | Neutralisation titer[1] | |
|---|---|---|
| | without Arildone | 1 µm/ml Arildone |
| 0 W | <2 | <2 |
| 1 W | 3.0 | 3.0 |
| 2 W | 2.5 | 4.0 |
| 3 W | 2.5 | 7.0 |
| 5 W | 4.5 | 6.5 |

[1] $^2$log serum dilution; mean titer for two monkeys.

TABLE H

Induction of neutralizing antibodies in rats by immunisation with virion polypeptides VP$_1$, VP$_2$, VP$_3$ of polio virus type 2 MEF$_1$

| Immunisation scheme | | | Neutralizing antibody titers | | |
|---|---|---|---|---|---|
| 0 W | 3 W | 8 W | 1.5 W | 4 W | 9 W |
| VP$_1$ + A + AlPO$_4$[3] | VP$_1$ + A | VP$_1$ | <1 | <1 | 6.0 |
| VP$_1$ + AlPO$_4$ | VP$_1$ | VP$_1$ | <1 | <1 | <1 |
| VP$_1$ + AlPO$_4$ | IDU[2] | — | <1 | 9.5 | n.t.[4] |
| VP$_2$ + A + AlPO$_4$ | VP$_2$ + A | VP$_2$ | <1 | <1 | 4.0 |
| VP$_2$ + AlPO$_4$ | VP$_2$ | VP$_2$ | <1 | <1 | <1 |
| VP$_2$ + AlPO$_4$ | IDU | — | <1 | 9.0 | n.t. |
| VP$_3$ + A + AlPO$_4$ | VP$_3$ + A | VP$_3$ | <1 | <1 | 4.0 |
| VP$_3$ + AlPO$_4$ | VP$_3$ | VP$_3$ | <1 | <1 | 2.0 |
| VP$_3$ + AlPO$_4$ | IDU | — | <1 | 9.5 | n.t. |
| IDU | VP$_1$ | — | 2.0 | 4.0 | n.t. |
| IDU | VP$_2$ | — | 4.0 | 4.0 | n.t. |
| IDU | VP$_3$ | — | 4.5 | 5.5 | n.t. |
| IDU | IDU | — | 6.5 | 9.0 | n.t. |

[1] $^2$log serum dilution; mean value for two rats
[2] IDU D-antigen type 2
[3] VP$_1$ + A + AlPO$_4$: VP$_1$ plus 1 µg/ml Arildone and 1.5 mg/ml AlPO$_4$
[4] n.t. = not tested.

EXAMPLE I

A concentrated purified polio virus suspension in medium 199, prepared according to the standard procedure in microcarrier cultures of primary or in vitro cultured monkey kidney cells (Van Wezel, A. L. (1978), Develop. biol. Standard, 41, 159–168), is inactivated with formalin 1:4000 during 13 days at 37° C. After inactivation 1 µg/ml of Arildone is added to the inactivated virus suspension. This is done by dissolving the Arildone in dimethylsulphoxide in a concentration of 10 mg/ml and diluting 1:1000 in medium 199. One hundred milliliters of the latter solution is added per 900 ml of the inactivated virus suspension.

EXAMPLE II

The process of example I is carried out with the difference that the 1:1000 diluted Arildone solution is added to the virus suspension before the addition of the formalin 1:4000. Table E shows that the presence of Arildone has practically no influence on the inactivation rate of the polio virus. This embodiment offers the advantage that the antigen is already stabilized during the inactivation.

EXAMPLE III

Polypeptides of polio virus type 2 are separated by means of discontinuous SDS-PAAGE according to the method of Laemmli (Nature 227, 680 (1970)). After this separation the polypeptides are eluted separately from the polyacrylamide gel with a buffered physiological salt solution pH 7. A suspension of aluminum phosphate is added to this solution to obtain a concentration of 1.5 mg/ml, and Arildone is added to obtain a concentration of 1 µg/ml.

As shown in table H these vaccines containing the individual peptides provoke neutralizing antibodies in rats. 9n

I claim:

1. Vaccine containing one or more picorna virus antigens in the form of inactivated picorna virus or virus polypeptide thereof, free from live virus and containing a stabilizingly effective amount of at least one compound of formula 1

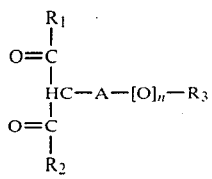

in which $R_1$ and $R_2$ each represent an alkyl or alkoxy group of not more than 6 carbon atoms, A represents a bivalent hydrocarbon radical of 3–12 carbon atoms, $R_3$ represents an unsubstituted or substituted phenyl radical and n represents one of the figures 0 or 1.

2. Vaccine according to claim 1, containing a compound of formula 1 in which $R_1$ and $R_2$ each represent an alkyl or alkoxy group of 1 or 2 carbon atoms, A represents a straight alkylene radical of 6 or 7 carbon atoms and $R_3$ represents a phenyl radical substituted with one or more halogen atoms, alkoxy or nitro groups.

3. Vaccine according to claim 2 containing a compound of formula 1 in which $R_1$ and $R_2$ each represent an ethyl radical. A represents the hexamethylene radical and $R_3$ represents the 2-chloro-4-methoxyphenyl radical.

4. Vaccine according to claim 1 containing at least 0.1 μg/ml of a compound of formula 1.

5. Vaccine according to claim 1 in which the antigens are present in the form of inactivated polio virus.

6. Vaccine according to claim 5, in which the antigens are present in the form of a mixture of inactivated polio virus of the strains Mahoney, $MEF_1$ and Saukett.

7. Vaccine according to claim 1, in which the antigens are present in the form of one or more picorna virus polypeptides.

8. Vaccine according to claim 7, in which the virus polypeptides are polio virus polypeptides $VP_1$, $VP_2$, $VP_3$ and/or $VP_4$.

9. In a process for adjuvanting a picorna virus vaccine the improvement which consists essentially of the steps of adding as a stabilizingly effective adjuvant a compound of formula 1 as defined in claim 1 to a suspension or solution of one or more inactivated picorna virus or virus polypeptide thereof antigens free from live virus.

10. The process of claim 9, characterized by adding a compound of formula 1 to obtain a concentration of at least 0.1 μg/ml.

11. The process of claim 9, characterized by adding a compound of formula 1 to a suspension of inactivated polio virus.

12. The process of claim 9, characterized by adding a compound of formula 1 to a suspension of live polio virus and inactivating the same.

13. The process of claim 9, characterized by adding a compound of formula 1 to a suspension of solution of one or more picorna virus polypeptides.

14. The process of claim 13, characterized in that the virus polypeptides are one or more of the polio virus polypeptides $VP_1$, $VP_2$, $VP_3$ and $VP_4$.

15. The process of claim 9 wherein in the compound of formula 1 $R_1$ and $R_2$ each represent an alkyl or alkoxy group of 1 or 2 carbon atoms, A represents a straight alkylene radical of 6 or 7 carbon atoms and $R_3$ represents a phenyl radical substituted with one or more halogen atoms, alkoxy or nitro groups.

16. The process of claim 15 wherein the compound of formula 1 $R_1$ and $R_2$ each represent an ethyl radical, A represents the hexamethylene radical and $R_3$ represents the 2-chloro-4-methoxyphenyl radical.

17. A vaccine according to claim 3 containing at least 0.1 μg/ml of a compound of formula 1.

18. A vaccine according to claim 1 which is a foot and mouth disease virus vaccine.

19. A vaccine according to claim 2 which is a foot and mouth disease virus vaccine.

20. A vaccine according to claim 3 which is a foot and mouth disease virus vaccine.

21. A process according to claim 9 wherein the vaccine is a foot and mouth disease vaccine.

22. A vaccine according to claim 2 which is a polio virus vaccine.

23. A vaccine according to claim 3 which is a polio virus vaccine.

24. In a process for adjuvanting a picorna virus vaccine, the improvement which consists essentially of the step of adding as a stabilizingly effective adjuvant a compound of formula 1 of claim 1 to a suspension or solution of one or more live virus antigens and inactivating the live virus.

* * * * *